US012605188B2

(12) United States Patent　　　　(10) Patent No.:　US 12,605,188 B2
Vitale et al.　　　　　　　　　　　　(45) Date of Patent:　　Apr. 21, 2026

(54) BONE ANCHORAGE SYSTEM AND SURGICAL METHODS FOR SAME

(71) Applicant: VERTEBRAL ANCHOR SYSTEMS, LLC, Irvington, NY (US)

(72) Inventors: Michael Vitale, Irvington, NY (US); Christopher S. Ahmad, New York, NY (US)

(73) Assignee: Vertebral Anchor Systems, LLC, Irvington, NY (US)

( * ) Notice: Subject to any disclaimer, the term of this patent is extended or adjusted under 35 U.S.C. 154(b) by 159 days.

(21) Appl. No.: 18/763,079

(22) Filed: Jul. 3, 2024

(65) Prior Publication Data

US 2024/0350174 A1　　Oct. 24, 2024

Related U.S. Application Data

(63) Continuation of application No. 17/956,680, filed on Sep. 29, 2022, now Pat. No. 12,053,208, which is a continuation of application No. 16/862,155, filed on Apr. 29, 2020, now Pat. No. 11,457,966, which is a continuation of application No. 16/486,342, filed as application No. PCT/US2017/049525 on Aug. 31, 2017, now Pat. No. 10,660,682.

(60) Provisional application No. 62/461,194, filed on Feb. 20, 2017.

(51) Int. Cl.
| | |
|---|---|
| *A61B 17/86* | (2006.01) |
| *A61B 17/68* | (2006.01) |
| *A61B 17/70* | (2006.01) |
| *A61B 17/80* | (2006.01) |
| *A61B 17/84* | (2006.01) |

(52) U.S. Cl.
CPC ............ *A61B 17/70* (2013.01); *A61B 17/683* (2013.01); *A61B 17/7053* (2013.01); *A61B 17/8052* (2013.01); *A61B 17/842* (2013.01); *A61B 17/864* (2013.01); *A61B 2017/681* (2013.01)

(58) Field of Classification Search
CPC .............................. A61B 17/70; A61B 17/864
See application file for complete search history.

(56) References Cited

U.S. PATENT DOCUMENTS

| | | | | | |
|---|---|---|---|---|---|
| 4,175,555 | A | * | 11/1979 | Herbert | ................ A61B 17/863 |
| | | | | | 606/304 |
| 5,782,831 | A | | 7/1998 | Sherman et al. | |
| 8,764,803 | B2 | | 7/2014 | Suddaby | |
| 8,870,869 | B2 | | 10/2014 | Meunier et al. | |
| 9,492,207 | B2 | | 11/2016 | Bacceli et al. | |
| 10,076,377 | B2 | | 9/2018 | Bonutti et al. | |
| 2002/0123751 | A1 | * | 9/2002 | Fallin | ..................... A61B 17/68 |
| | | | | | 606/331 |
| 2003/0088251 | A1 | * | 5/2003 | Braun | ................ A61B 17/7083 |
| | | | | | 606/279 |
| 2007/0260248 | A1 | * | 11/2007 | Tipirneni | ............. A61B 17/683 |
| | | | | | 606/65 |
| 2009/0149890 | A1 | * | 6/2009 | Martin | ............... A61B 17/1728 |
| | | | | | 606/301 |

(Continued)

*Primary Examiner* — Christian A Sevilla

(74) *Attorney, Agent, or Firm* — Corner Counsel, LLC

(57) ABSTRACT

A bone anchoring system having a flexible member with a first end and a second end opposite the first end. A fastener provided at a first end of the flexible member for retaining the flexible member within a bone. A rigid member is provided to ensure movement or pull-through of the flexible member does not occur.

9 Claims, 11 Drawing Sheets

(56)                  References Cited

U.S. PATENT DOCUMENTS

| | | | |
|---|---|---|---|
| 2009/0248077 A1 | 10/2009 | Johns | |
| 2011/0034925 A1 | 2/2011 | Tipirneni et al. | |
| 2012/0150231 A1 | 6/2012 | Alamin et al. | |
| 2012/0316606 A1* | 12/2012 | Farin | A61B 17/8685 |
| | | | 606/305 |
| 2014/0155944 A1* | 6/2014 | Truman | A61B 17/844 |
| | | | 606/328 |
| 2015/0305780 A1 | 10/2015 | Carlson et al. | |
| 2016/0022323 A1* | 1/2016 | Seme | A61B 17/7022 |
| | | | 606/263 |

* cited by examiner

BONE ANCHORAGE SYSTEM AND SURGICAL METHODS FOR SAME

CROSS-REFERENCE TO RELATED APPLICATIONS

This application is a continuation of and claims priority to U.S. patent application Ser. No. 17/956,680 which is a continuation of U.S. patent application Ser. No. 16/862,155 filed on Apr. 29, 2020 now U.S. Pat. No. 11,457,966 which is a continuation of U.S. patent application Ser. No. 16/486, 342, which is a national phase filing under 35 U.S.C. 371 of International Patent Application No. PCT/US17/49525 filed on Aug. 31, 2017 now U.S. Pat. No. 10,660,682 which claims priority to U.S. Provisional Application Ser. No. 62/461,194 filed Feb. 20, 2017, all of which are hereby fully incorporated by reference in their entireties as if fully set forth herein.

FIELD OF INVENTION

The present invention relates to bone anchorage systems and, more particularly, to bone anchorage systems utilizing one or more points of fixation.

BACKGROUND OF THE INVENTION

Certain defects and injuries of the skeletal system can be ameliorated with the use of bone anchorage systems that promote corrective bone healing. This process often utilizes one or more rigid fixators, such as for example rods for spinal columns, and bone plates for long bones, attached to bones, to provide stability to the bones to enable desired healing. The connection of anchorage systems to the bones may be facilitated with bone screws, as well as tensile tape or tethers. Heretofore known devices and methods of using bone anchorage systems are known to those skilled in the art to exhibit certain shortcomings including excessive rigidity, propensity for pulling out from bone, or weakening, as well as other destabilizations of fixation, leading to suboptimal healing and possible corrective surgeries.

Far cortex anchoring systems are a family of bony anchors, delivery modalities and other bony fixation systems which allow for three-dimensional control of skeletal structures, thereby providing the ability to control deformity and instability, and guide healing and growth. Far cortex fixation provides reduced stiffness of the anchoring system compared to near cortex fixation. While one application of far cortex fixation is designed for spinal fixation, far cortex fixation can also be applied to the appendicular skeleton (e.g., as a ligament augmentation around the knee, foot or toe). In spinal fixation, far cortex fixation systems are also known as vertebral anchoring systems ("VAS"). VAS can be used with both fusion and non-fusion applications. In each of these, the approach can be anterior, posterior, or lateral, unilateral or bilateral, and can function independently or as an adjunct to a limited fusion procedure.

Certain defects of the spine can benefit greatly from use of VAS. For instance, scoliosis, which is an excessive spinal curvature in the coronal plane, and hyperkyphosis, which is an excessive anterior spinal curvature in the sagittal plane, can be targets for VAS correction. When correcting such defects, the VAS is configured to provide a translational force to the affected vertebrae to maintain coronal and sagittal balance. In certain pathoanatomies, the spine may exhibit an axial rotation of the vertebrae. To correct an axial rotation, the VAS is configured to provide a rotational force to the affected vertebrae. This is accomplished by creating a VAS that is anchored to the far cortex of the vertebra. The surgeon can vary the moment arm created by the VAS to optimize translational and rotational forces for the requisite correction.

For defects affecting the growing spine, such as, for example, adolescent idiopathic scoliosis, corrections must be revisited often to ensure the translational and rotational, where necessary, forces are optimized. Continual iterative correction requires convenient access to the corrective construct to reduce the stress on the patient caused by multiple surgical entries. The VAS is provided with a mechanism capable of providing rapid access and ease of iterative correction to reduce such stress.

Other potential injuries, such as, for example, proximal junctional kyphosis ("PJK"), may arise as a consequence of previous corrective spinal surgeries. PJK occurs at the vertebra adjacent a conventional corrective construct. PJK may lead to proximal junctional failure ("PJF"). While PJK can be treated with revision surgery, the VAS construct can provide stability to the vertebra adjacent the uppermost vertebra connected to the construct to limit or prevent PJK, thereby reducing the need for additional surgery.

SUMMARY OF THE INVENTION

In an embodiment, the present invention relates to a bone anchoring system including a flexible member with a first end and a second end opposite the first end, a fixation element connected to the first end of the flexible member, a rigid member configured to be disposed adjacent a bone interface, the rigid member being capable of withstanding lateral tension applied via the flexible member, the flexible member being configured to fail prior to failure of the rigid member, and a tensioning mechanism coupled with the flexible member, the tensioning mechanism being capable of providing fixation to the flexible member with limited access.

In an embodiment of the bone anchoring system, the rigid member is a cannulated bone screw. In another embodiment of the bone anchoring system, the rigid member is a grommet.

In an embodiment of the bone anchoring system, the flexible member travels in a transverse direction to a vertebra for at least a portion of the flexible member proximate the first end of the flexible member. In another embodiment of the bone anchoring system, the flexible member travels from the cortical bone of a pedicle of a patient's vertebral body towards a far cortical bone of a lateral aspect of the patient's vertebral body.

In an embodiment of the bone anchoring system, the fastener is selected from the group consisting of a grommet, a cortical button, a toggle and a reverse locking plate.

In an embodiment of the bone anchoring system, the bone anchor system also includes a cannulated bone screw capable of receiving the flexible member therein.

In an embodiment of the bone anchoring system, the tensioning mechanism includes a self-ratcheting tightening mechanism. In another embodiment of the bone anchoring system, the tensioning mechanism is a fixation collar. In a further embodiment of the bone anchoring system, the fixation collar includes a base portion and two arms extending from the base portion, a slot located on each of the two arms, and each of the slots are configured to receive the flexible member therein.

In an embodiment, the present invention relates to a vertebral anchoring system including a flexible member having a first end and a second end opposite the first end, the flexible member being capable of being positioned transversely across a vertebra, a fixation element connected to the first end of the flexible member, a rigid member disposed adjacent an interface between the vertebra and the flexible member, the rigid member being capable of withstanding lateral tension applied via the flexible member, the flexible member being configured to fail prior to failure of the rigid member, an axial rod positioned exterior to a vertebra, and a coupler capable of coupling the flexible member to the rod.

In an embodiment of the vertebral anchoring system, the rigid member is a cannulated screw enclosing at least a portion of the flexible member. In another embodiment of the vertebral anchoring system, the rigid member is a grommet.

In an embodiment of the vertebral anchoring system, the flexible member travels in a transverse direction to a vertebra for at least a portion of the flexible member proximate the first end of the flexible member. In another embodiment of the vertebral anchoring system, the flexible member travels from the cortical bone of a pedicle of a patient's vertebral body towards a far cortical bone of a lateral aspect of the patient's vertebral body. In another embodiment of the vertebral anchoring system, the flexible member travels from one a first pedicle of a patient to a point anterior of the vertebral foramen of the patient and then towards a second pedicle of the patient.

In an embodiment of the vertebral anchoring system, the fixation element is selected from the group consisting of a grommet, a cortical button and a toggle.

In an embodiment of the vertebral anchoring system, the coupler is a fixation collar. In a further embodiment of the vertebral anchoring system, the fixation collar includes a base portion and two arms extending from the base portion, a slot located on each of the two arms, and each of the slots are configured to receive the flexible member therein. In another embodiment of the vertebral anchoring system, the coupler is a self-ratcheting collar.

BRIEF DESCRIPTION OF DRAWINGS

The accompanying drawings, which are incorporated in, and constitute a part of, the specification, illustrate embodiments of the invention and, together with the description, serve to explain the objects, advantages, and principles of the invention.

DETAILED DESCRIPTION OF THE INVENTION

The present disclosure involves devices and methods for the far cortex fixation of fractured bones, as well as devices and methods for the far cortex fixation of spinal deformities that enable a surgeon to apply leverage to vertebral bodies to promote a rotation or a translation or a combination of both to the vertebral bodies.

Those skilled in the art will recognize that various terms are used broadly and may encompass various differences within a group of specific elements. For instance, the term "bone screw" is used to encompass pedicle screws, reduction screws, compression screws and the like. Those skilled in the art will recognize that these screws can be used interchangeably to the extent possible according to the invention.

Figures 1, 2:
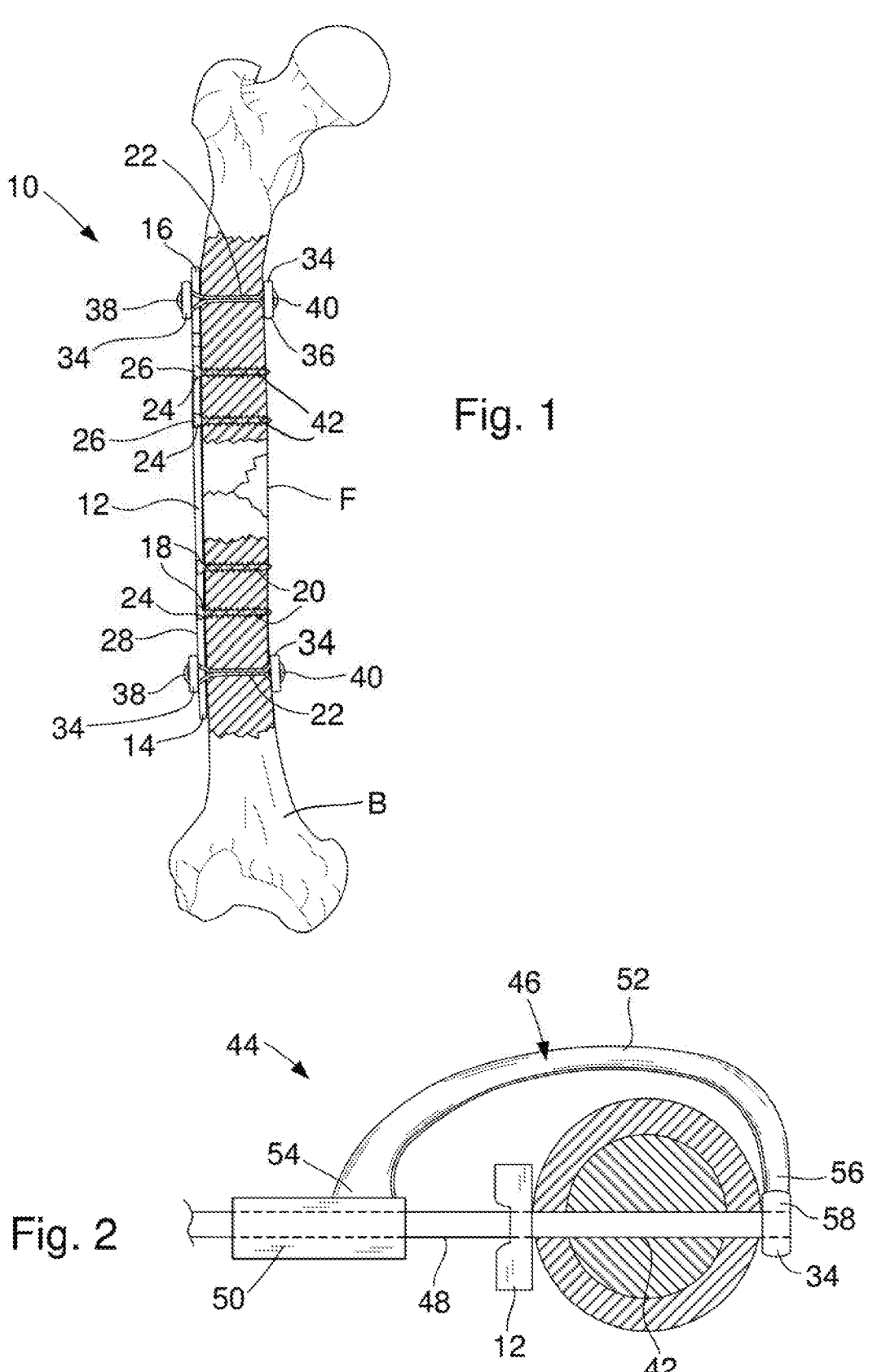
FIG. 1 is a cross-sectional view of a bone anchoring system attached to a femur in accordance with an exemplary embodiment of the present invention.
FIG. 2 is a top view of a targeting guide for attaching a bone anchoring system to a long bone shown in section, in accordance with an exemplary embodiment of the present invention.

Referring now to an embodiment of the invention in more detail, FIG. 1 depicts a bone anchorage system 10 configured to repair a long bone fracture F. The depicted bone B is a femur, but is readily understood to represent any long bone. The bone anchorage system 10 includes a plate 12 configured to span the fracture F. The plate 12 is generally elongate in shape and includes a first end 14 and a second end 16 opposite the first end 14. The plate 12 may have a length such that the first end 14 and the second end 16 extend a distance beyond the fracture F to provide additional support and fixation to the system 10. The plate 12 further includes a plurality of fixation element receiving through-holes 18 configured to receive various fixation elements, such as, for example, bone screws 20 or flexible members 22, spaced along the length of the plate 12. The receiving holes 18 may be oriented along the plate 12 in various arrangements, including on or near a center line passing through the longitudinal axis of the plate 12. At least one of the plurality of receiving holes 18 is located proximate the first end 14 of the plate 12 and at least another one of the plurality of receiving holes 18 is located proximate the second end 16 of the plate 12. This ensures that fixation occurs adjacent and on opposite sides of the fracture F.

The receiving holes 18 may be polyaxial, thereby enabling one or more bone screws 20 to be introduced at a variety of angles. A surgeon may employ one or more various angles of entry for the bone screws 20 along the length of the plate 12 as necessary. Such decision may be made by the surgeon during implantation of the bone anchorage system 10. The receiving holes 18 may include recesses 24 configured to accept a head portion 26 of the bone screw 20 so that the head portion 26 of the bone screw 20 is flush with a top side 28 of the plate 12 when inserted therein.

The flexible member 22 may comprise a high-tension suture or high-tension tape, or any other thin elongate member known in the art that is capable of withstanding tensile stress. The flexible member 22 is passed through a fixation element 34 positioned adjacent the far cortex of the bone and then retrieved and retracted towards the near cortex of the bone, as will be described in more detail below. In one embodiment, the fixation element 34 is a cortical button. In other embodiments, the fixation element 34 can be a reverse locking plate 36 or any other fixation element known in the art, such as a grommet or toggle. Once secured to the patient, the flexible member 22 includes a proximate end 38 and a distal end 40 opposite the proximate end 38.

In an embodiment, the flexible member 22 extends between two fixation elements 34 and is attached to one fixation element 34 at the proximate end 38 of the flexible member 22 and another fixation element 34 at the distal end 40 of the flexible member 22.

Figure 3:
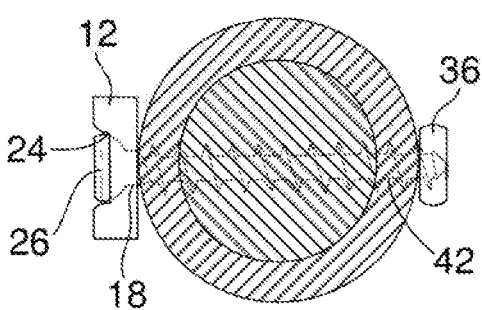
FIG. 3 is a cross-sectional view of a bone anchoring system attached to a long bone shown in section in accordance with an exemplary embodiment of the present invention.
Figure 4:
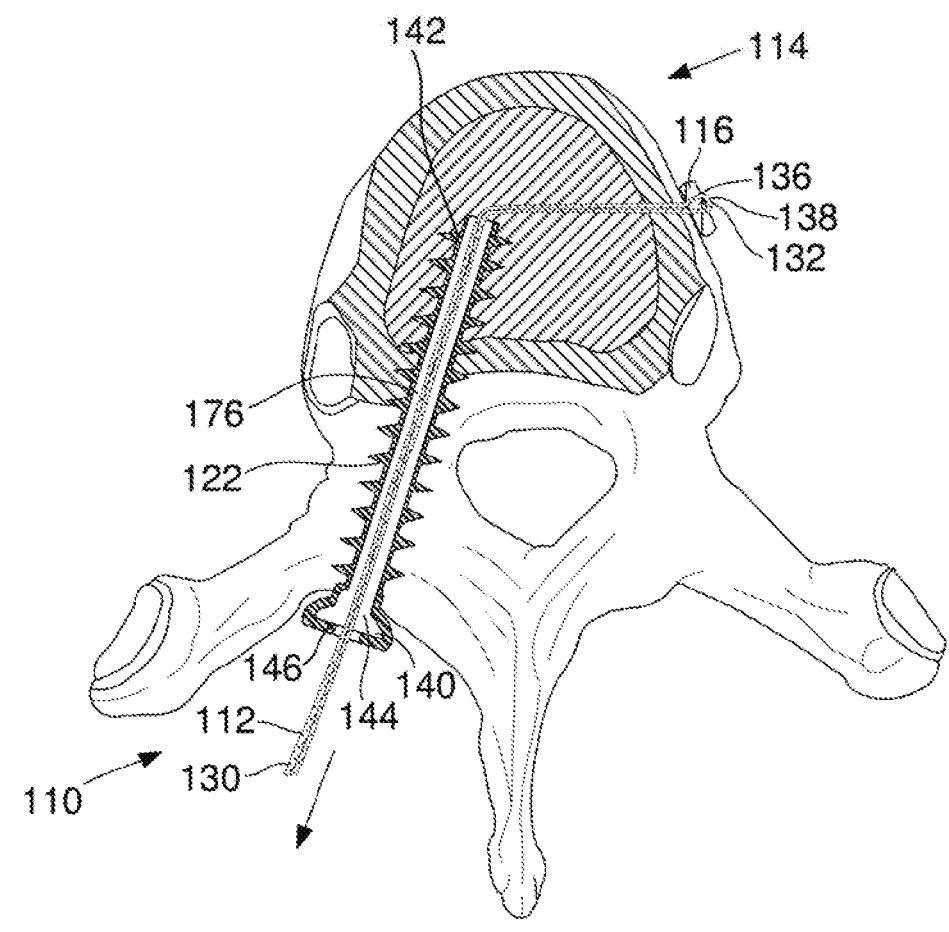
FIG. 4 is a cross-sectional view of a vertebral anchoring system, implanted in a vertebral body shown in partial section, in accordance with an exemplary embodiment of the present invention.

In another embodiment, the flexible member 22 and the fixation element 34 connected to the proximate end 38 of the flexible member 22 is replaced with the screw 20. The fixation element 34 connected to the distal end 40 is replaced with a reverse locking plate 36. The screw 20 extends from the plate 12 through the far cortex of the bone to a reverse locking plate 36 having interior threads (not shown) and is threadably engaged therewith (see FIG. 3).

The fixation element 34 may be secured opposite the plate 12 by utilizing a variety of techniques. In a first method, the fixation element 34 is configured with a width and depth smaller than the diameter of a bone tunnel 42 that is pre-drilled through the bone. The fixation element 34 also has a width and depth smaller than the diameter of the receiving holes 18 in the plate 12. The length of the fixation element 34 is longer than the diameter of the holes 18. In this configuration, the fixation element 34 may be pre-threaded with the flexible member 22 and then passed through the holes 18 in the plate 12 and through the bone tunnel 42. (See FIG. 2.) After exiting the far cortex of the bone, the fixation element 34 may be rotated and retracted against the bone so as to be flush against the bone, thereby preventing the fixation element 34 from escaping through the bone or the holes 18.

Turning to FIG. 2, a targeting guide 44 provides a second method for introducing the system 10 to a patient. The targeting guide 44 includes an arm 46 that arcuately extends exteriorly to the bone of a patient to the far cortex opposite the plate 12. In use, the arm 46 releasably retains the fixation element 34 against the bone so that a shuttle 48 carrying the flexible member 22 can be passed through the bone tunnel 42 and the fixation element 34. The shuttle 48 then carries the flexible member 22 in a reverse direction to return the flexible member 22 through the bone tunnel 42 and the holes 18.

The targeting guide 44 may include a cannulated handle 50 that permits the introduction of multiple tools therethrough. A C-shaped arm 52 having a proximate end 54 and a distal end 56 opposite the proximate end 54 extends arcuately from the handle 50 to the far cortex of the bone. The targeting guide 44 includes a locking mechanism 58 that releasably locks the fixation element 34 to the distal end 56 of the C-shaped arm 52 (see FIG. 2). The guide 44 may include a release (not shown) on a proximate end 54 of the handle 50, enabling release of the fixation element 34 or reverse locking plate 36 after the flexible member 22 or the screw 20, respectively, is attached thereto.

FIGS. 4-14 depict an alternative embodiment of the present invention known as a vertebral anchoring system 110 ("VAS"). Generally, various embodiments of the VAS 110 according to the present invention include a flexible member 112 capable of imparting a translational force or a rotational force or both to a vertebral body 114. The flexible member 112 can be introduced into the vertebral body 114 from various approaches and can be anchored to various points within the vertebral body 114. The vertebral body 114 is typically pre-drilled to facilitate delivery of the flexible member 112 therethrough, as will be described in more detail below. The flexible member 112 is anchored to the far cortex of vertebral body 114 via a fixation element 116. The flexible member 112 is then anchored to a rigid fixator 118 via a fixation collar 120 (see FIG. 10). In various embodiments, a cannulated bone screw 122 or a stress-shielding grommet 124 is included to shield the flexible member 112 from direct contact with the cortical bone.

With particular reference to FIGS. 4-7, the flexible member 112 includes a leading end 126 and a tail end 128. The leading end 126 is passed through the fixation element 116 positioned adjacent the far cortex of the bone and then retrieved and retracted towards the near cortex of the vertebral body 114. Once secured to the rigid fixator 118, the flexible member 112 includes a proximate end 130 and a distal end 132 opposite the proximate end 130. Far cortex fixation of the VAS 110 is achieved exterior to the vertebral body 114 via the fixation element 116. In an embodiment, fixation element 116 is a cortical button. In other embodiments, fixation element 116 may be substituted by a reverse locking plate 134 (see FIG. 13) or any other fixation element known in the art.

The flexible member 112 is preferably a high-tensile suture or high-tensile tape, or any other thin elongate member known in the art that can withstand a sufficient tensile stress to survive ratcheting or tensioning of the VAS. Biomechanically, the flexible member 112 is designed to fail prior to loads that would cause bony plowing as a safeguard against neurological injury. That is, the flexible member 112 is designed and constructed to rupture or break when subjected to forces that would approach but not be sufficient to cause the flexible member 112 to travel laterally into the cortical bone or otherwise cut through the cortical bone. Similarly, the flexible member 112 is designed and constructed to fail at loads prior to those which would cause either the bone screw 122 or the grommet 124 to fail. This is especially important for the spinal area as the spinal cord is located within the vertebral body 114.

The flexible member 112 must also have sufficient tensile durability to allow the flexible member 112 to be pulled taut and self-ratcheted or fixed by friction in the fixation collar 120 after fixation to the far cortex of the vertebral body 114 at the distal end 132 of the flexible member 112. The flexible member 112 can transmit an effective moment force to the vertebral body 114 to either cause a translation or rotation or both of the vertebral body 114. The flexible member 112 must also be of sufficient durability to retain its tensile strength after the proximate end 130 of the flexible member 112 is connected to the rigid fixator 118.

Figures 7, 8, 9:
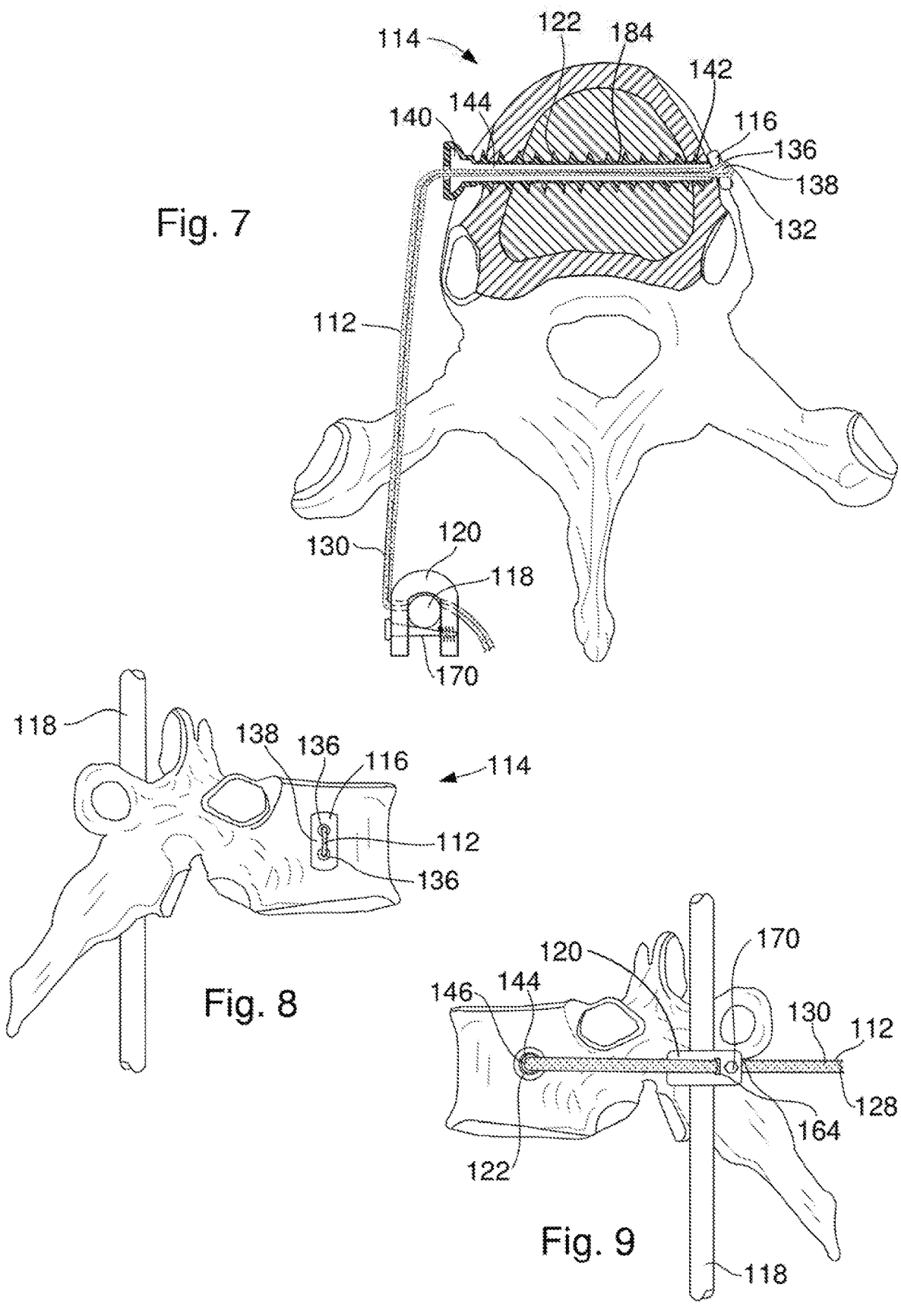
FIG. 7 is a partial cross-sectional view of a vertebral anchoring system, connected to a vertebral body shown in partial section, in accordance with an exemplary embodiment of the present invention.
FIG. 8 is a side view of the vertebral anchoring system of FIG. 7.
FIG. 9 is an opposite side view of the vertebral anchoring system of FIG. 7.

Referring now to FIGS. 8 and 9, in an embodiment, the fixation element 116 is generally rectangular in shape and includes at least two openings 136 separated by a central post 138. The flexible member 112 is threaded through the two openings 136 of the fixation element 116. Such threading involves passing the flexible member 112 through one of the openings 136, over the post 138 and then passing the flexible member 112 through the other of the openings 136 in the reverse direction. This allows the flexible member 112 to transfer sufficient force to the central post 138 to retain the fixation element 116 in place against the far cortex of the vertebral body 114. In this configuration, the flexible member 112 is free to slide through the fixation element 116 in either direction until the leading end 126 of the flexible member 112 is secured to the rigid fixator 118.

Optionally, a cannulated bone screw 122 may be introduced to the vertebral body 114 at the proximate end 130 of the flexible member 112. The bone screw 122 includes a proximate end 140 and a distal end 142 opposite the proximate end 140 and a channel 144 extending therebetween. The channel 144 of the bone screw 122 is configured to house the flexible member 112 therein. In this embodiment, the bone screw 122 acts as a barrier between the flexible member 112 and the cortical bone of the vertebral body 114, thereby shielding the flexible member 112 and minimizing the possibility of the flexible member 112 cutting through the cortical bone of the vertebral body 114. In an embodiment, the bone screw 122 is configured with a rounded proximate edge 146 to reduce the frictional force on the flexible member 112 to minimize the possibility that the flexible member 112 will fail after installation due to shearing thereof. The degree of curvature of the rounded proximate edge 146 may be varied to optimize moment arm while reducing stress on the flexible member 112.

The cannulated screws 122 may be configured to be flush with the surface of the vertebral body 114 when inserted, or they may be configured to extend beyond the surface of the vertebral body 114 to increase the length of the moment arm. The screw 122 may be made of any material suitable for implantation. The outer surface of the screw 122 or any portion thereof may be porous to allow bone ingrowth. The outer surface may also be coated with a bone growth promoting material. The proximate end 140 of the screw 122 may include structure that permits a tool to be inserted internally to cause rotation, or the screw 122 may have external structure to communicate with a tool to cause rotational insertion of the screw when the flexible member is already inserted therethrough.

Figures 14, 15, 16:
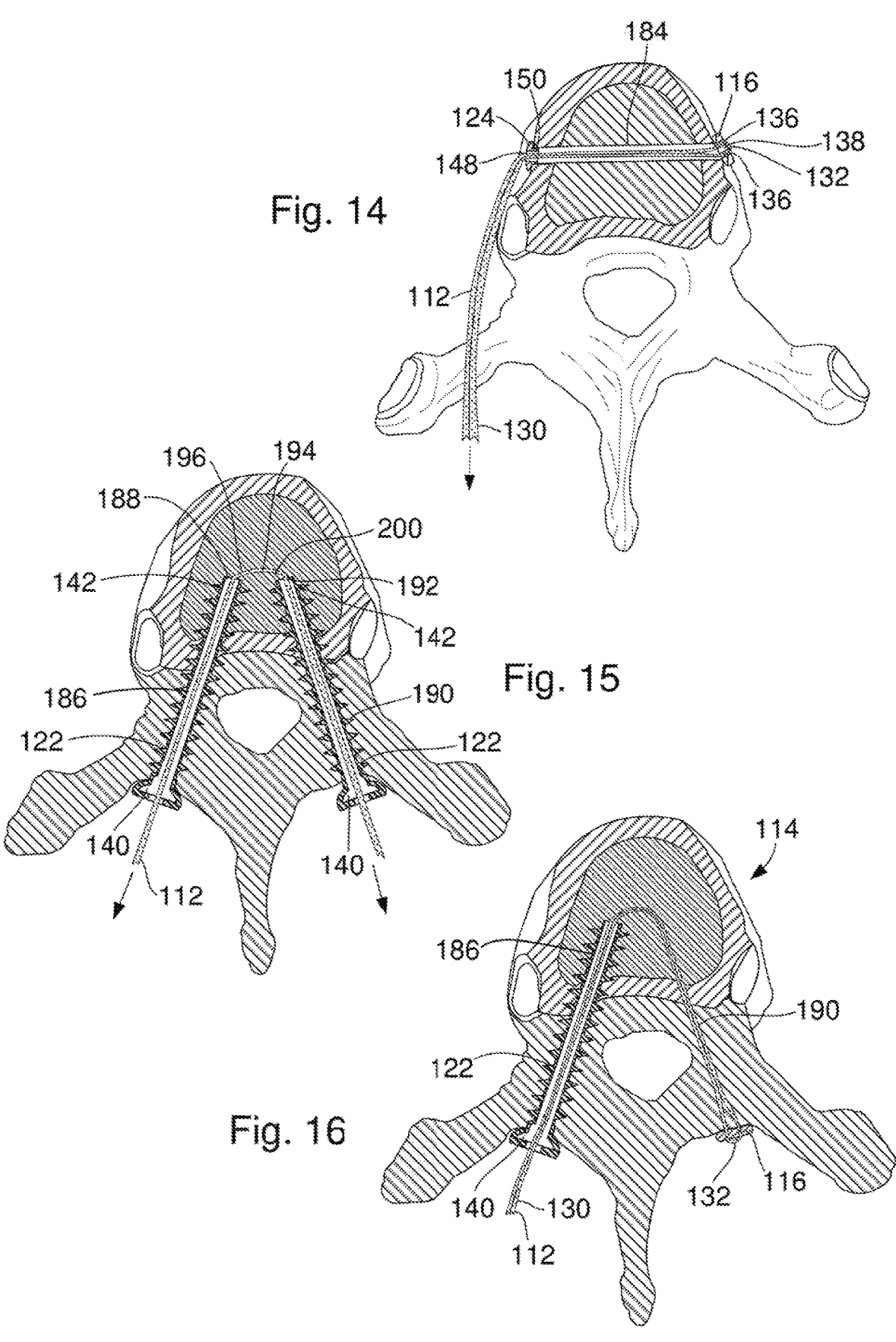
FIG. 14 is a cross-sectional top view of a vertebral anchoring system, connected to a vertebral body shown in partial section, in accordance with an exemplary embodiment of the present invention.
FIG. 15 is a cross-sectional top view of a vertebral anchoring system, implanted in a vertebral body shown in partial section, in accordance with an exemplary embodiment of the present invention.
FIG. 16 is a cross-sectional top view of a vertebral anchoring system, implanted in a vertebral body shown in partial section, in accordance with an exemplary embodiment of the present invention.

In alternative embodiments, as depicted in FIG. 14, the bone screw 122 is replaced by a specialized grommet 124 configured to prevent cut-through of the flexible member 112. The grommet 124 is located at the cortical bone interface near the proximate end 130 of the flexible member 112. The grommet 124 acts as a barrier between the flexible member 112 and the cortical bone of the vertebral body 114, thereby minimizing the possibility of the flexible member 112 cutting through the cortical bone of the vertebral body 114. The grommet 124 includes a rounded inner diameter 148 configured to reduce frictional force on the flexible member 112. The grommet 124 may also have a thickness 150 designed to optimize moment arm while further reducing stress on the flexible member 112.

Figures 10, 11:
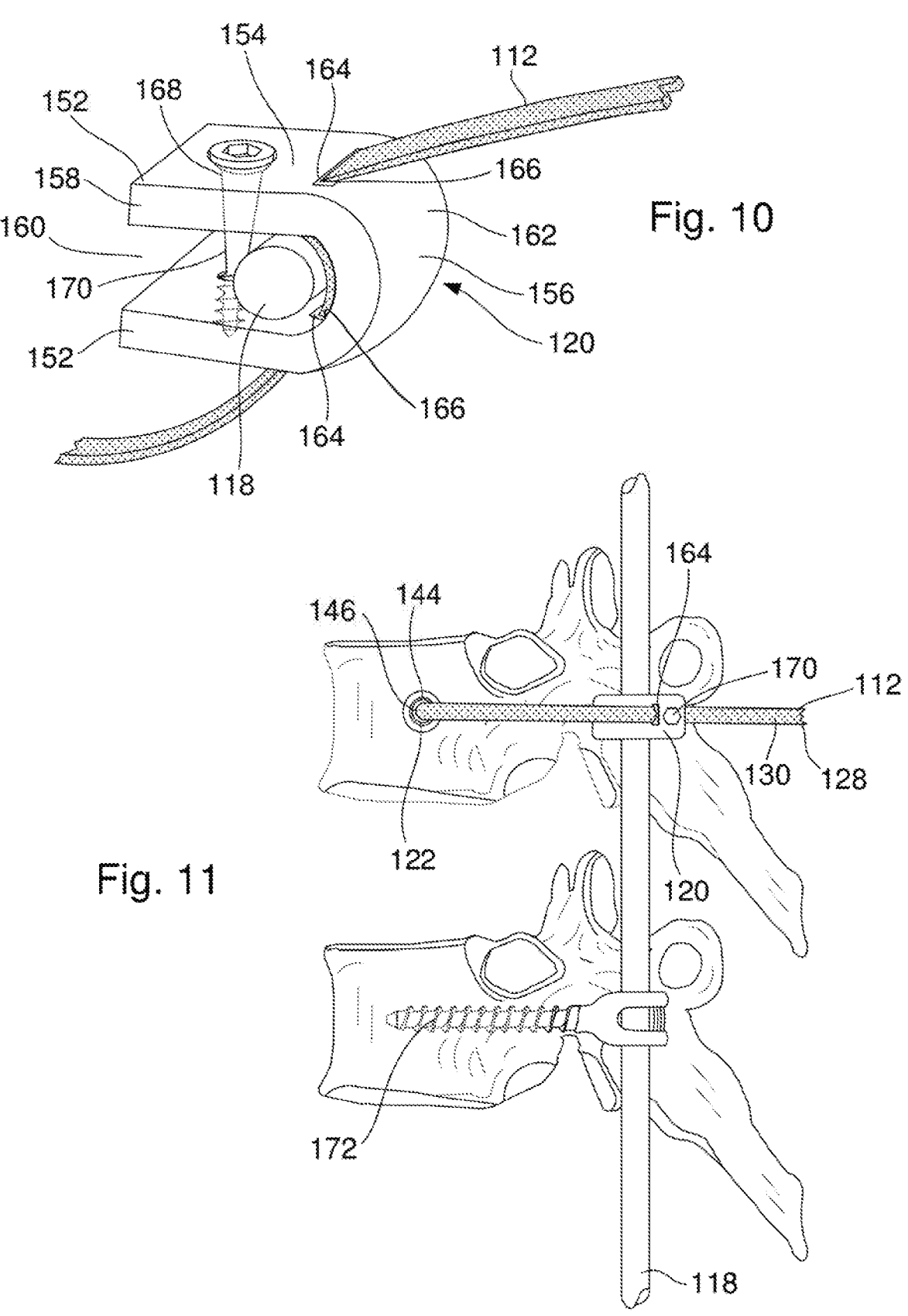
FIG. 10 is a perspective view of a collar for use with a vertebral anchoring system in accordance with an exemplary embodiment of the present invention.
FIG. 11 is a side view of a vertebral anchoring system in accordance with an exemplary embodiment of the present invention.

With reference to FIGS. 9-11, the fixation collar 120 connects the flexible member 112 to the rigid fixator 118. The collar 120 is generally U-shaped with two arms 152 having proximate ends 154 proximate a base portion 156 and distal ends 158 opposite the base portion 156. The collar 120 further includes an interior portion 160 and an outer wall 162. The collar 120 may include a pair of slots 164 adjacent the proximate end 154 of each of the two arms 152. The slots 164 are sized and shaped to receive the flexible member 112 therethrough and to pass the flexible member 112 between the interior portion 160 of the collar 120 and the rigid fixator 118. The slots 164 preferably have a smooth outer perimeter 166 so that frictional forces on the flexible member 112 are minimized. Each of the two arms 152 of the collar 120 may also include a cut-out 168 adjacent the distal ends 158 thereof. The cut-out 168 is configured to receive a locking element 170. In an embodiment, the locking element 170 may be a compression screw with a diameter that increases along its length from tip to head.

In use, the flexible member 112 is passed through the slots 164 of the collar 120. This may occur prior to or after mounting the collar 120 on the rigid fixator 118. Once properly mounted, the desired tension is applied to the flexible member 112. While maintaining the desired tension, the locking element 170 is introduced to the cut-outs 168 of the collar 120 and fixed therein, thereby locking the flexible member 112 in place with pressure applied to the flexible member 112 between the rigid fixator 118 and the collar 120. Once introduced, the flexible member 112 can be easily re-tensioned by further retracting the flexible member 112 and re-tightening the locking element 170 as necessary.

Those skilled in the art will recognize that alternative means of retaining tension on the flexible member 112 are possible. For instance, the collar 120 may include an external attachment for the flexible member and an internal rotational ratcheting mechanism, wherein the internal rotational ratcheting mechanism is rigidly attached to the rigid fixator 118. In use, after the flexible member 112 is attached, the external attachment of the collar 120 is rotated about the internal rotational ratcheting mechanism until the desired tension in the flexible member 112 is reached. Alternatively, the collar 120 may include a passage having a spring-loaded pawl that permits insertion of the flexible member 112, but prevents withdrawal of the flexible member 112. Such a configuration would permit the surgeon to simply insert the flexible member 112 through the passage and apply tension to the flexible member 112 until the desired rotational and translational force is achieved. Once the surgeon releases the flexible member 112, the collar 120 would maintain the position of the flexible member 112 without requiring the surgeon to maintain the tension while the locking element 170 is inserted to retain the flexible member 112.

Figures 12, 13:
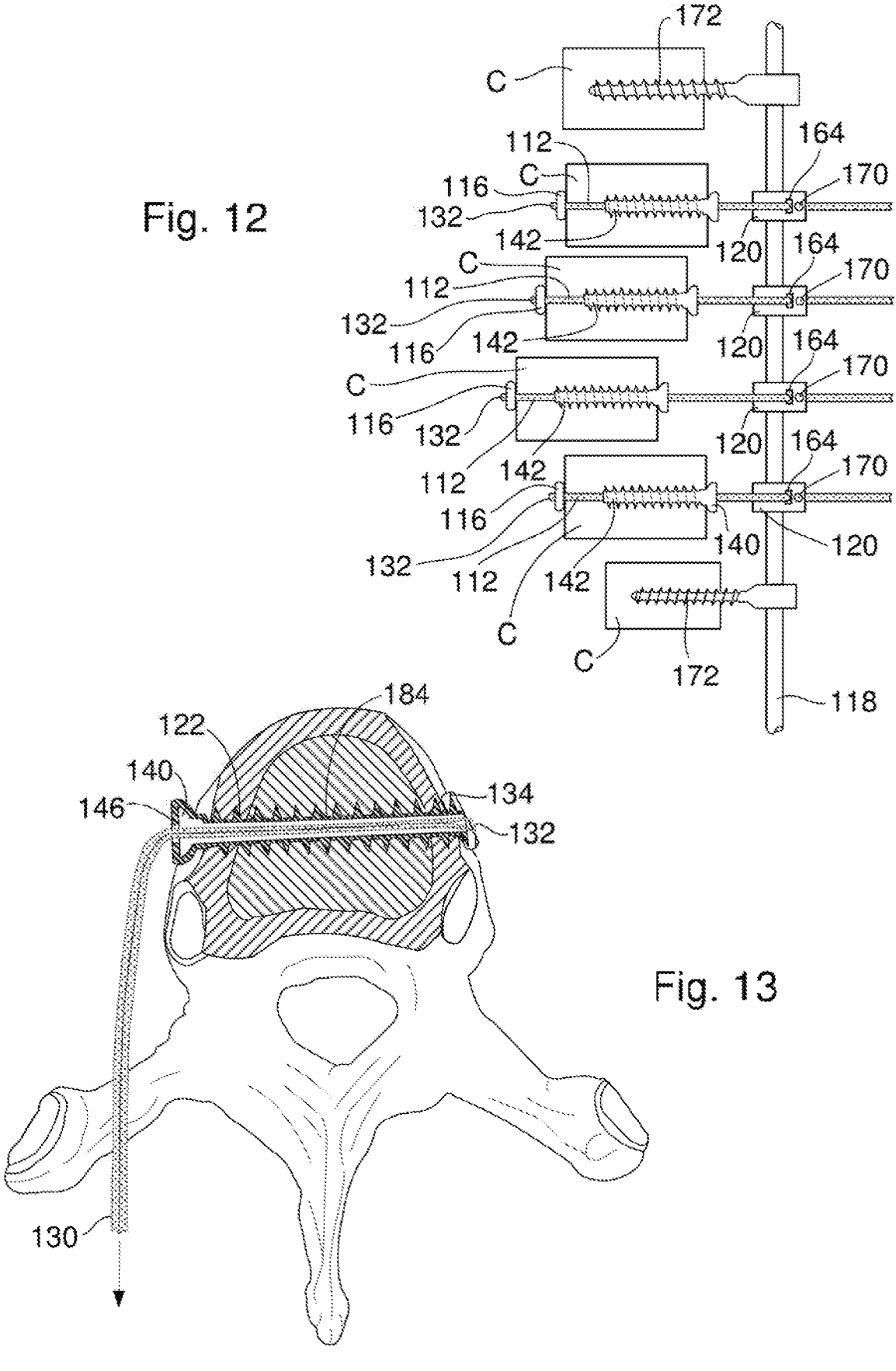
FIG. 12 is a side view of a vertebral anchoring system in accordance with an exemplary embodiment of the present invention.
FIG. 13 is a cross-sectional top view of a vertebral anchoring system, implanted in a vertebral body shown in partial section, in accordance with an exemplary embodiment of the present invention.

The collar 120 is extremely helpful when using multi-level VAS for the apical correction of kyphosis. With particular reference to FIG. 12, in this method, traditional anchors 172 are used at either end of a plurality of vertebra C to be corrected. The two traditional anchors 172 are then connected to the rigid fixator 118. The VAS 110 is then attached to each level between the traditional anchors 172. The collars 120 would then allow the surgeon to quickly make incremental adjustments at each level, and then iteratively repeat the process at each level with minimal time or effort expended.

The biomechanics and moment arm of the VAS is ideally suited to counter the translations which result from the pathoanatomies of various spinal defects such as, for example, adolescent idiopathic scoliosis, among others. The translations being rotation, lordosis and lateral deviation. As such, it is optimal to use a limited number of VAS attachments to obtain optimum apical correction while including a link to a longer more traditional construct in the form of the rigid fixator 118, for example. The unique self-ratcheting mechanism can be used to tighten the flexible member 112 allowing fixation with limited access.

Figures 5, 6:
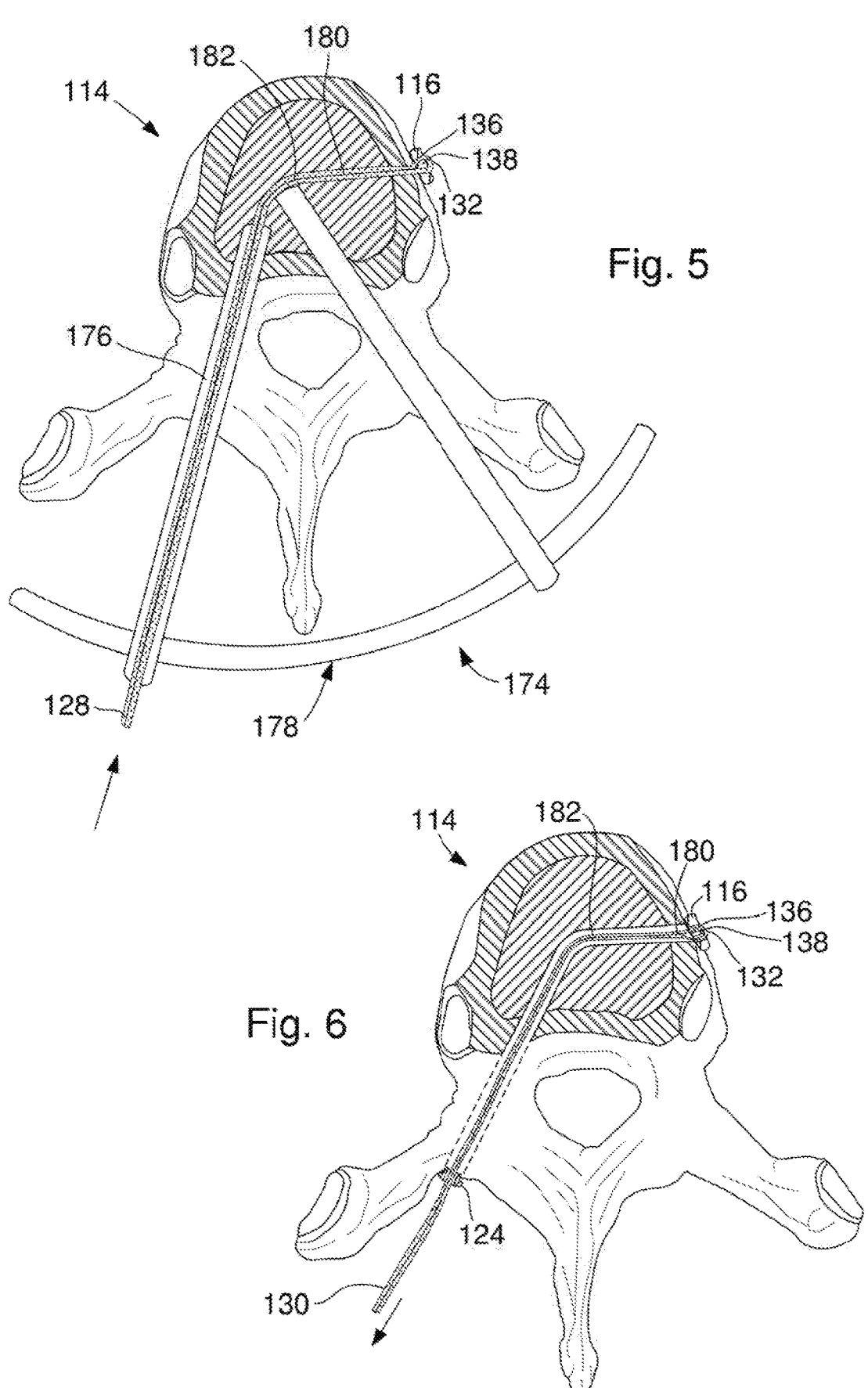
FIG. 5 is a partial cross-sectional view of a surgical guide tool, in use with a vertebral body shown in partial section, in accordance with an exemplary embodiment of the present invention.
FIG. 6 is a cross-sectional view of a vertebral anchoring system, in use with a vertebral body shown in partial section, in accordance with an exemplary embodiment of the present invention.

Turning now to implantation of the VAS, in an embodiment, vertebral anchoring is achieved through a transpedicular approach via a flexible member delivery system 174 (see FIG. 5). The flexible member delivery system 174 allows for passing the flexible member 112 through the near cortex at the introduction site, through the cancellous bone tissue within the vertebral body 114 and then through the far cortex of the vertebral body 114. This is accomplished by first accessing the posterior aspect of the vertebral body 114. Next, a pedicular channel 176 is drilled through the pedicle into the vertebral body 114 extends at least to a point that is anterior to the vertebral foramen. A surgical guide tool 178, or "SGT" for short, is then introduced into the pedicular channel 176 to provide alignment for a cutting tool to create an opening 180 extending from the lateral aspect of the vertebral body 114 to the pedicular channel 176, thereby creating a transpedicular channel 182 that extends from the near cortex at a pedicle to the far cortex at a lateral aspect of the vertebral body 114. The cutting tool may be any conventional cutting tool known in the art such as, for example, a bone drill.

The flexible member delivery system 174 also provides for threading the flexible member 112 through the two openings 136 of the fixation element 116, and then passing the flexible member 112 back through the cancellous bone tissue and the cortical bone at the introduction site. Optionally, the bone screw 122 or the grommet 124 may be introduced either before or after introduction of the flexible member 112. As will be understood by those skilled in the art, conventional procedures typically utilize a cortical-cancellous installation. However, optimal fixation and moment arm is achieved through a bicortical, or cortical-cancellous-cortical, installation.

Alternatively, the transpedicular channel 182 may be created with a flexible drill bit and an arcuate jig. Such an apparatus would enable the surgeon to create a curved path from the pedicle to the far cortex lateral aspect in one step. Thus, reducing the number of entries required to create the transpedicular channel 182. Optionally, the jig may include a physical stop to prevent over drilling.

After the transpedicular channel 182 has been created in the vertebral body 114, the flexible member 112 may be inserted directly therethrough. In an embodiment, the cannulated screw 122 may then be inserted therein. In another embodiment, the cannulated screw 122 may be inserted with the flexible member 112 passed therethrough. Alternatively, the cannulated screw 122 may be replaced by the grommet 124. A targeting guide may be utilized to hold a fixation element 116 over the opening 180 adjacent the far cortex lateral aspect of the vertebral body 114 enabling the surgeon to attach the flexible member 112 thereto. After the flexible member 112 is secured to the fixation element 116, the flexible member 112 is passed in a reverse direction out through the introduction site. Thereafter, the surgeon may attach the free leading end 126 of the flexible member 112 to the rigid fixator 118 located exterior the vertebral body 114 via the fixation collar 120. The rigid fixator 118 may be anchored to other vertebra as necessary. Depending on the angle of correction between the rigid fixator 118 and the vertebral body 114, applying tension to the flexible member 112 may affect a rotation or translation or both on the vertebral body 114.

In certain situations, a transvertebral approach (see FIGS. 7, 13 and 14) may be used to produce a maximum moment arm to effect maximum axial rotation. In this method, a transvertebral channel 184 is created laterally between the lateral aspects of the vertebral body 114 at a location anterior to the vertebral foramen using a bone drill or other conventional tool known in the art. After the transvertebral channel 184 has been created, the flexible member 112 may be inserted directly through the transvertebral channel 184. The cannulated screw 122 may be inserted through the vertebral body 114 with the flexible member 112 passed through the screw 122. Alternatively, the flexible member 112 may be inserted through the transvertebral channel 184 prior to insertion of the cannulated screw 122. Alternatively, the cannulated screw 122 may be replaced by the grommet 124. A targeting guide may be utilized to hold fixation element 116 over the transvertebral channel 184 adjacent the far cortex lateral aspect of the vertebral body 114 enabling the surgeon to attach the flexible member 112 thereto. After the flexible member 112 is secured to the fixation element 116, the flexible member 112 is passed in a reverse direction out through the introduction site. Thereafter, the surgeon may attach the free leading end 126 of the flexible member 112 to the rigid fixator 118 located exterior the vertebral body 114 via the fixation collar 120. The rigid fixator 118 may be anchored to other vertebra as necessary. Depending on the angle of correction between the rigid fixator 118 and the vertebral body 114, applying tension to the flexible member 112 may affect a rotation or translation or both on the vertebral body 114. This approach reduces the amount of pre-drilling necessary as only one transvertebral channel 184 is required.

Referring now to FIGS. 15 and 16, in another embodiment, the VAS may be utilized in a pedicle-to-pedicle configuration. In this configuration, a first pedicular channel 186 having a distal end 188 and a second pedicular channel 190 having a distal end 192 are drilled into the flexible member 112 at least to a point that is anterior to the vertebral foramen according to conventional methods known in the art (see FIG. 16). The first pedicular channel 186 is drilled through one of the pedicles of the vertebral body 114 while the second pedicular channel 190 is drilled through the other pedicle of the vertebral body 114. A transvertebral channel 194 intersecting the pedicular channels 186, 190 is then drilled through the vertebra by methods known to those skilled in the art. The transvertebral channel 194 extends laterally between the lateral aspects the vertebral body 114 and intersects the distal ends 188, 192 of the two pedicular channels 186, 190 and forming a generally U-shaped channel 196. Optionally, after creating the generally U-shaped channel 196, cannulated screws 122 may be inserted into one or both of the pedicular channels 186, 190. As described above, the screws 122 serve to protect the flexible member 112 from frictional forces caused by rubbing of the flexible member 112 along the cortical bone. As will be evident to one of ordinary skill in the art, the surgeon can modify the force applied to the vertebra by modifying the angle of introduction of the screws 122.

After the generally U-shaped channel 196 has been formed, the flexible member 112 may be routed therethrough using a shuttle (not shown) to guide the flexible member 112 down the first pedicular channel 186, and the SGT 178 to guide the flexible member 112 through the portion of the transvertebral channel 194 extending between the two pedicular channels 186, 190. The flexible member 112 may be retrieved from the distal end 192 of the second pedicular channel 190 with a crochet-type hook (not shown), or any other means known in the art.

Alternatively, the leading end 126 of the flexible member 112 may comprise a semi-rigid material with a tip that is bullet-shaped to aid in insertion. The tip may be configured with a curvature to one side. Such a configuration would permit the surgeon to insert the flexible member 112 into the first pedicular channel 186 until the tip of the flexible member 112 reaches the transvertebral channel 194. Further insertion of the flexible member 112 would force the tip against a far wall 200 of the transvertebral channel 194, which would then force the tip to angle towards the second pedicular channel 190. Additional insertion of the flexible member 112 would result in the tip curling towards the second pedicular channel 190. Continued pressure would advance the flexible member 112 across the transvertebral channel 194 until the tip bends into the second pedicular channel 190. Further pressure would cause the tip to advance through and out of the second pedicular channel 190. Such a configuration would enable quick insertion of the flexible member 112 without the need for tools.

Alternatively, the two pedicular channels 186, 190 may be created at angles such that the distal ends 188, 192 of the pedicular channels 186, 190 intersect at a location anterior to the vertebral foramen (see FIG. 16). In either pedicle-to-pedicle configuration, the surgeon may use one, two, or zero cannulated screws 122, and one or zero fixation elements 116. As will be evident to one of ordinary skill in the art, this concept of pedicle-to-pedicle vertebral anchoring could also be applied to the growing spine to tether the apex of the patient's scoliotic curvature and allow continued iterative and gradual correction.

Referring now to FIGS. 17-21, the present disclosure also provides a method for preventing proximal junctional kyphosis. This method includes inserting a pair of translaminar screws 202 each having a proximate end 204 and a distal end 206 opposite the proximate end 204. The translaminar screws 202 may have a flexible member 112 attached to the proximate ends 204 of the screws 202 via any conventional means known in the art.

Figures 17, 18:
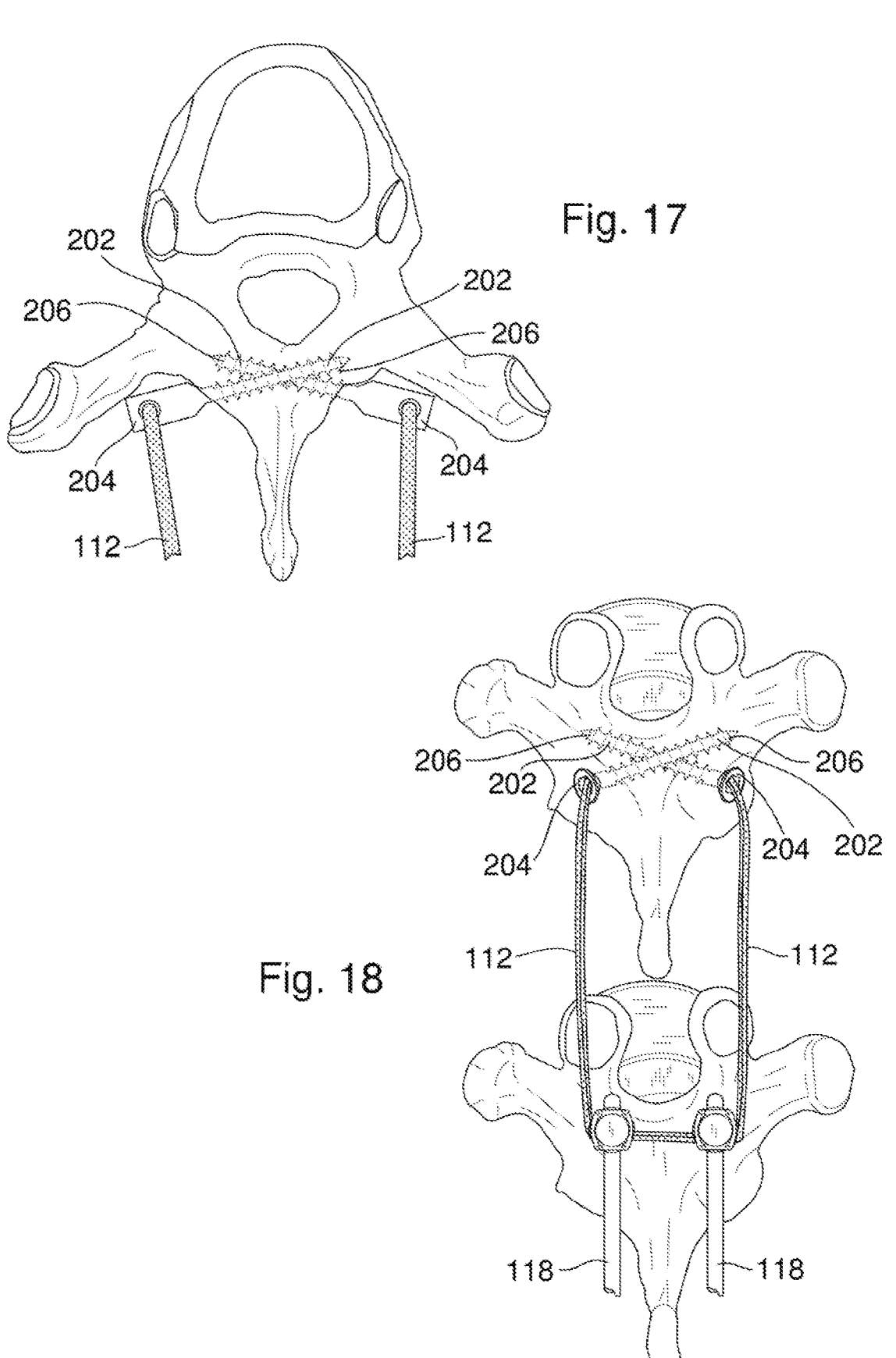
FIG. 17 is a top view of a vertebral anchoring system, connected to a vertebral body shown in partial section, in accordance with an exemplary embodiment of the present invention.
FIG. 18 is an exaggerated rear perspective view of a vertebral anchoring system, connected to a pair of adjacent vertebral bodies, in accordance with an exemplary embodiment of the present invention.
Figures 19, 20:
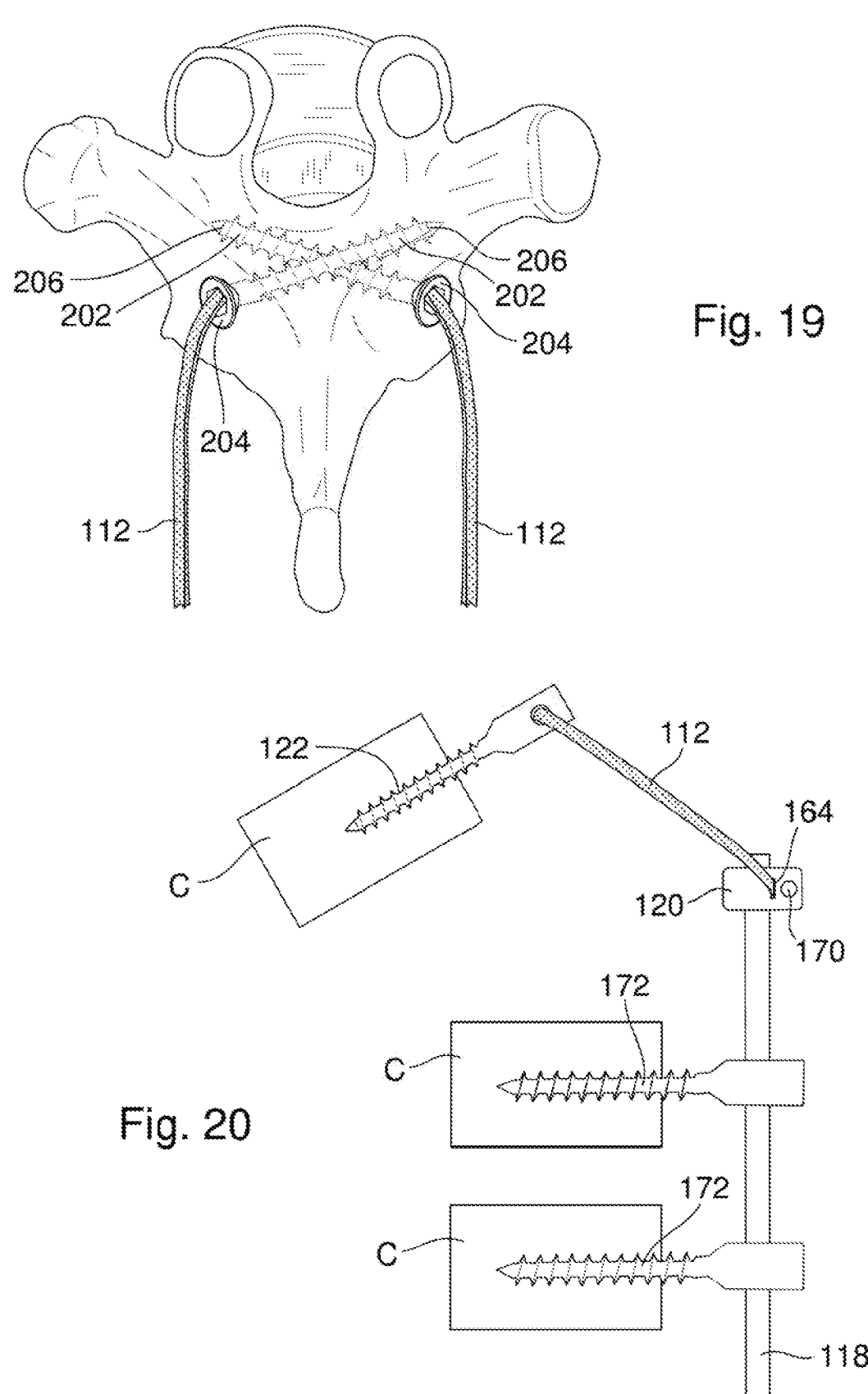
FIG. 19 is a top view of a vertebral anchoring system, connected to a vertebral body shown in partial section, in accordance with an exemplary embodiment of the present invention.
FIG. 20 is a side view of a vertebral anchoring system in accordance with an exemplary embodiment of the present invention.
Figure 21:
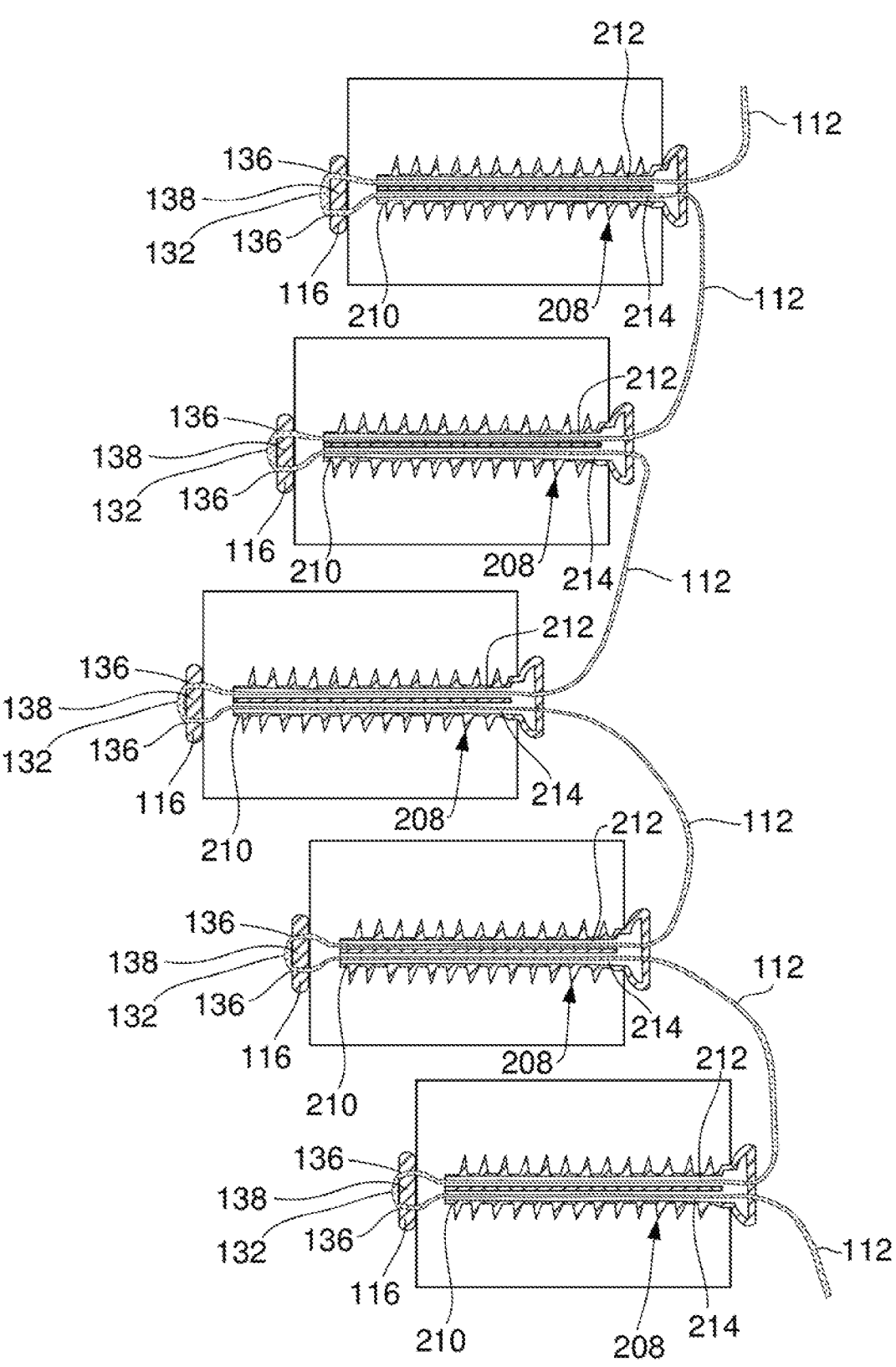
FIG. 21 is a cross-sectional side view of a vertebral anchoring system in accordance with an exemplary embodiment of the present invention.

Referring to FIG. 18, which is a posterior view of two adjacent vertebrae exaggerated to aid understanding of the invention and is not an accurate depiction of the relevant vertebral anatomy, the flexible member 112 is connected to a rigid fixator 118 attached to an adjacent vertebra. The flexible member 112 may have some limited elasticity, thereby permitting some minimal movement at that joint, but preventing proximal junction failure.

Figure 22:
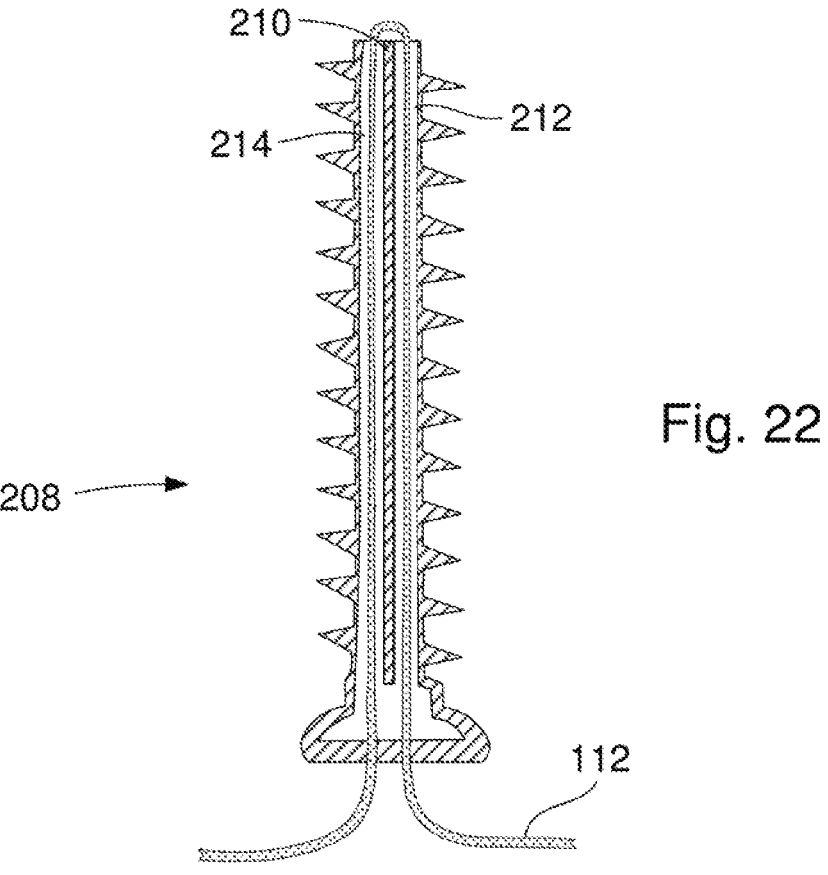
FIG. 22 is a longitudinal-sectional top view of a dual channel cannulated screw in accordance with an exemplary embodiment of the present invention.
Figure 23:
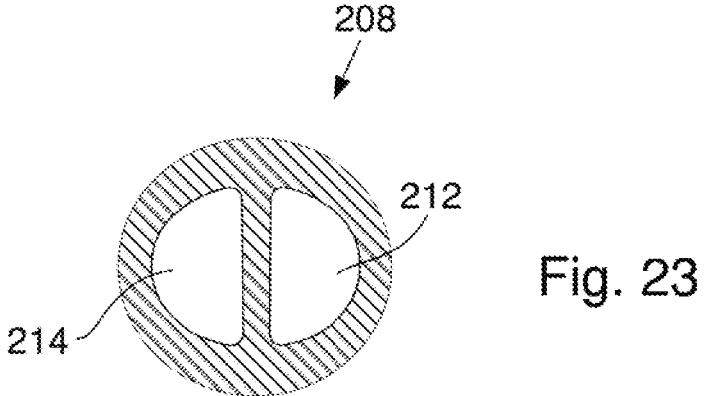
FIG. 23 is a cross-sectional view of the dual channel cannulated screw of FIG. 22.

Turning to FIGS. 22 and 23, the VAS may also be used to tether any number of vertebra to one another. This tethering may be done posteriorly, anteriorly, or translaterally. The tethering may utilize a dual channel screw 208 connected to the fixation element 116 at a distal end 210 of the dual channel screw 208. The dual channel screw 208 permits the flexible member 112 to be routed down a first channel 212, through one opening 136 in the fixation element 116, back through the other opening 136 in the fixation element 116, and back through the second channel 214 in the screw 208. Alternatively, a dual channel sleeve may be used instead of the dual channel screw 208

Various modifications may be made to the scope of the present invention without departing from the spirit thereof. For instance, the cannulated screws 122 need not be screws. They may be linearly inserted sleeves. The sleeves may include any type of exterior surface configuration that aids in the retention of the sleeve within the vertebra, such as, toothing or knurling.

The fixation element 116 may also be modified to include a spring-loaded pawl that permits the flexible member 112 to be inserted therein, but prevents the withdrawal thereof. Such an apparatus would enable the surgeon to attach the flexible member 112 to the fixation element 116 with very limited access to the side of the bone where the fixation element 116 would be located. In this configuration, while not necessary, it would be helpful to include a series of teeth on the flexible member 112 to be engaged by the pawl.

Other embodiments of the invention will be apparent to those skilled in the art from consideration of the specification and practice of the invention disclosed herein. It is intended that the embodiments described below be considered as exemplary only, with a true scope and spirit of the invention being indicated by the appended claims. Moreover, none of the features disclosed in this specification should be construed as essential elements, and therefore, no disclosed features should be construed as being part of the claimed invention unless the features are specifically recited in the claims. In addition, it should be understood that any of the features disclosed on any particular embodiment may be incorporated in whole or in part on any of the other disclosed embodiments.

What is claimed is:
1. A vertebral tethering system comprising:
a first cannulated screw having a first end and a second end, the first cannulated screw positioned at a first location on a first vertebra, a fixation element positioned at a second location on a periphery of the first vertebra;
a second cannulated screw having a first end and a second end, the second cannulated screw positioned at a first location on a second vertebra, a fixation element positioned at a second location on a periphery of the second vertebra, a flexible member having a proximal portion and a distal portion positioned to extend through the first cannulated screw to the first fixation element and through the second cannulated screw and second fixation element, a tensioning mechanism positioned to engage the flexible member enabling the flexible member to be tensioned and secured in place for tethering the first and second vertebra together.

2. The vertebral tethering system of claim 1, wherein the first fixation element is positioned at an outer cortex of the first vertebral body of the vertebra.

3. The vertebral tethering system of claim 2, wherein the first fixation element is positioned near a pedicle of the first vertebra.

4. The vertebral tethering system of claim 1, wherein the first and second cannulated screws each include a first and second channels within the cannulation.

5. The vertebral adjustment system of claim 4 wherein the first and second fixation elements each include first and second openings.

6. The vertebral adjustment system of claim 1, wherein the first cannulated bone screw penetrates a pedicle of the first vertebra and the second cannulated bone screw penetrates the pedicle of the second vertebra.

7. The vertebral adjustment system of claim 1, wherein the first cannulated bone screw penetrates an outer cortex of the first vertebral body of the vertebra and the second cannulated bone screw penetrates an outer cortex of the second vertebral body of the vertebra.

8. The vertebral adjustment system of claim 4, wherein the proximal portion of the flexible member is position so as to extend from the first end of the first cannulated screw through its first channel through the first vertebra and through the first opening in the fixation element and into the second opening of the first fixation element, through the vertebra and into the second channel of the first cannulated screw exiting the first end of the first cannulated screw, then into the first end of the second cannulated screw through its first channel, through the second vertebra into the first opening of the second fixation element and into the second opening of the second fixation element through the vertebra and the second channel of the second cannulated screw and exterior of the first end of the second cannulated screw, wherein the distal portion of the flexible member is exterior of the first end of the first cannulated screw and the proximal end of the flexible member is exterior of the first end of the second cannulated screw.

9. A cannulated screw for use in spinal fixation having a first head end and a second end longitudinally separated by an externally threaded shaft, the shaft is cannulated forming a passageway from the first head end to the second end, the passageway comprising first and second channels separated by a common wall.

* * * * *